United States Patent [19]

Cantrell

[11] Patent Number: 4,504,473

[45] Date of Patent: Mar. 12, 1985

[54] PYRIDINE SOLUBLE EXTRACT OF A MICROORGANISM

[75] Inventor: John L. Cantrell, Hamilton, Mont.

[73] Assignee: Ribi ImmunoChem Research, Inc., Hamilton, Mont.

[21] Appl. No.: 600,605

[22] Filed: Apr. 17, 1984

Related U.S. Application Data

[63] Continuation of Ser. No. 393,823, Jun. 30, 1982, abandoned.

[51] Int. Cl.³ .............................................. A61K 35/78
[52] U.S. Cl. .................................................. 424/195.1
[58] Field of Search .......................................... 424/195

[56] References Cited

U.S. PATENT DOCUMENTS

| | | | |
|---|---|---|---|
| 3,956,481 | 5/1976 | Jolles et al. | 424/92 |
| 3,976,544 | 8/1976 | Adam et al. | 424/92 |

OTHER PUBLICATIONS

Meyer et al., J. Natl. Can. Inst. 52: 103–108, 1974.
Ribi et al., Natl. Can. Inst., Monograph, No. 39, 1974.
Rozencweig et al., Canc., 40: 334–342, 1977.
Pharmacological Basis of Cancer Chem., Williams & Wilkins Co., 1975, pp. 245–270.

*Primary Examiner*—Jerome D. Goldberg
*Assistant Examiner*—John W. Rollins
*Attorney, Agent, or Firm*—Burgess, Ryan & Wayne

[57] ABSTRACT

A pharmaceutical composition is disclosed comprising a purified pyridine-soluble extract obtained from microorganism which contains between about 7 and 20% by weight of protein, between about 10 and 16% by weight of sugar, and between about 35 and 55% by weight of fatty acids which when combined with trehalose dimycolate and an acetone precipitated by-product of endotoxic glycol lipids extracted with chloroform-methanol in a pharmaceutically acceptable medium is useful as an anti-animal tumor agent in the treatment of animals.

7 Claims, No Drawings

PYRIDINE SOLUBLE EXTRACT OF A MICROORGANISM

This application is a continuation of application Ser. No. 393,823, filed June 30, 1982, now abandoned.

BACKGROUND OF THE INVENTION

The present invention is directed to a pyridine-soluble extract of a microorganism which, when combined with trehalose dimycolate (TDM) and an acetone precipitated by-product of endotoxic glycolipids extracted with chloroform-methanol (ACP), provides a pharmaceutical composition possessing anti-animal tumor properties.

Bacteria such as *Corynebacterium parvum* have been the subject of experimental work to isolate and characterize the component responsible for inducing inhibition of tumor growth [see, for example, *Anti Tumor Activity and Lymphoreticular Stimulation Properties of Fractions Isolated from C. parvum;* Cantrell, et al. Cancer Research 39, pgs. 3554–3563 (September, 1979)]. Apart from anti-tumor activity, *C. parvum* has shown to be a potent stimulator of the lymphoreticular system resulting in undesirable increases in spleen and liver weights and blastogenesis. Applicant has discovered that a pyridine-soluble extract of a microorganism possesses potent anti-animal tumor properties without the undesirable toxic effects associated with the prior art products.

Trehalose dimycolates (TDM), may be obtained from organisms such as, for example, *M. avium, M. phlei, M. tuberculosis* (Strain H 37 RV and Ayoma B), *M. bovis* BCG, *M. smegmatis, M. kansasii, Nocardia rubra, M. bovinis* and *Corynebacterium diphtheriae.*

Bacteria such as *M. avium* are grown, harvested and then heat killed. The cell mass is then extracted with several solvents and then an active, solvent soluble, fraction is extracted. This extract is further purified by a series of solvent extractions to provide crude TDM (See *Biologically Active Components from Mycobacterial Cell Walls. I. Isolation and Composition of Cell Wall Skeleton and Component P3;* Azuma, et al., Journal of the National Cancer Institute, Volume 52, pgs. 95–101, 1974) incorporated herein by reference. As disclosed in Azuma et al., crude TDM may then be further purified by centrifugal microparticulate silica gel chromatography to give purified TDM.

An acetone precipitated by-product of endotoxic glycolipids extracted with chloroform-methanol (ACP) does not possess tumor-regressive properties when used alone or in combination with trehalose dimycolate. For a more complete discussion of ACP, its properties and methods of production, reference is made to *Peptides as Requirement for Immunotherapy of the Guinea-Pig Line-10 Tumor with Endotoxins;* Ribi, et al, Cancer Immunol. Immunother., Volume 7, pgs. 43–58 (1979) incorporated herein by reference. ACP can be prepared from any Enterobacteriaciae including, but not limited to, the following genera: Salmonella, Shigella, Escherichia, Brucella, Bordetella, Citrobacter, Pseudomnas, Pasturella, Neisseria, Proteus, Klebsiella, and Serratia.

The following species are typically employed: *S. minnesota, S. typhimurium, B. pertussis, B. abortus, S. enteritidis, E. coli, S. typhi, S. marcescens, S. typhosa, Shigella flexni,* and *S. abortus equi.*

It is, therefore, an object of the present invention to provide a pharmaceutical composition containing a pyridine-soluble extract of a microorganism in combination with trehalose dimycolate and an acetone-precipitated by-product of (ACP) endotoxic glycolipids extracted with chloroform-methanol.

It is another object of the invention to provide a method of treating animal tumors in warm blooded animals using the composition containing the pyridine-soluble extract of a microorganism, TDM and ACP.

SUMMARY OF THE INVENTION

The present invention relates to pharmaceutical compositions comprising a pyridine-soluble extract of a microorganism containing between about 7 and 20% by weight of protein about 10 to 16% by weight of sugar, and about 35 to 55% by weight of fatty acids, in combination with TDM and ACP. The pyridine soluble extract preferably contains about 12% by weight of each of protein and sugar and about 45% by weight of fatty acids.

Any microorganism may be used to obtain the pyridine-soluble extract including, for example, *M. bovis* BCG, *M. phlei, M.smegmatis, M. kansasii, Nocardia rubra, Corynebacterium diphtheriae* and *Corynebacterium parvum. Corynebacterium parvum* is especially preferred.

Whole cells of the bacteria preferably in the form of a paste, are mixed with pyridine. The resulting mixture is separated to obtain a supernatant fraction which contains the pyridine-soluble extract and a pyridine residue. Optionally, the pyridine residue may be subjected to repeated separation procedures as described above using pyridine to remove further quantities of the desired extract.

The pyridine is then removed from the extract and the dried extract is dialyzed against a suitable liquid such as distilled water. The absence of whole cells or cell fragment contaminants is confirmed by electron microscopy. The resulting purified extract may then be lyophilized by known methods to obtain a stable product.

The pyridine-soluble extract produced in accordance with this invention may be combined with TDM and ACP to produce a composition having potent anti-animal tumor activity without stimulating the induction of spleen and liver enlargements. The cancers which may be treated by this composition include animal tumors such as bovine squamous cell carcinoma, bovine fibrosarcoma, equine sarcoid, equine melanoma, equine squamous cell carcinoma, canine mammary tumors, canine adenoma and canine melanoma.

The composition is preferably administered by injection in a pharmaceutically acceptable medium such as an oil-droplet emulsion directly into the tumor under conditions more particularly described below. The aforesaid composition may be stabilized as, for example, by a lyophilization procedure and then reconstituted without loss of potency.

The amount of the pyridine-soluble extract in a single injection for the treatment of animals is between about 375 and 2500 micrograms/milliliter. The amount of each of TDM and ACP is between about 375 and 1250 micrograms/milliliter.

The number of milliliters of the biologic injected into the tumor is determined by the size of the tumor in accordance with the following table:

| Animal Dosage According to Tumor Size | |
| --- | --- |
| Diameter of Tumor (cm) | Amount of Biologic Injected (ml) |
| 0–1 | up to 0.5 |
| 1–2 | 0.5 to 2.5 |
| 2–3 | 2.5 to 5 |
| 3–5 | 5 to 10 |
| 5–8 | 10 to 15 |
| greater than 8 | 15 to 20 |

The maximum dose per injection is about 40 milligrams for the pyridine-soluble extract, about 6 milligrams for TDM and about 20 milligrams for ACP. The course of treatment comprises up to six injections administered at about two week intervals.

The present composition in a suitable injection medium such as an oil-droplet emulsion is administered directly into tumors. The amount of the pyridine-soluble extract in a single injection is between about 200 and 5000 micrograms, preferably between about 800 and 1200 micrograms. The amount of TDM is between about 50 and 1000 micrograms and the amount of ACP is between about 150 and 1000 micrograms. The preferred single dosage level for each of TDM and ACP is between about 475 and 525 micrograms. All of the above-mentioned dosage levels are based on a typical 70 kilogram adult animal. The injections are administered about once every week for up to a total of 15 injections.

As described above, the composition for treatment of warm blooded animals may be used in the form of an oil droplet emulsion. The amount of oil used is in the range of between about 0.5 and 3.0 percent by volume based on the total volume of the composition. It is preferred to use between about 0.75 and 1.5 percent by volume of the oil. Examples of such oils include light mineral oil, squalane, squalene, and 7-n-hexyloctadecane.

The homogenized oil containing mixture is then combined with a detergent which may optionally be dissolved in a saline solution prior to mixing. The amount of detergent is typically between about 0.02 and 0.25 percent by volume and preferably between about 0.10 and 0.20 percent by volume based on the total volume of the composition. Any common detergent material may be used including Tween-80 and Arlacel (produced by the Atlas Chemical Company).

The mixture resulting from the addition of detergent is then homogenized to form a suspension which has a high percentage of oil droplets coated with the active components as determined by observation under a microscope.

The following examples are for illustrative purposes only and are not intended to limit or in any way redefine the invention as claimed in the claims appended hereto.

EXAMPLE 1

Preparation of Pyridine-Soluble Extract from *Corynebacterium Parvum*

*Corynebacterium parvum* (*P. acnes*, Strain 4182) was grown and harvested at 37° C. in NIH thioglycolate broth for between 48 and 72 hours to obtain a whole cell paste. The paste was then washed with 500 ml. of distilled water. 90 grams (wet weight) of the washed paste was mixed with 200 ml. of neat pyridine and centrifuged at 1700×g for one hour at 4° C. A pyridine-soluble extract was removed as a supernatant fraction. The remaining residue was extracted with additional pyridine under identical conditions as described above.

Following filtration, using Whatman No. 1 paper, the pyridine extracts were pooled and the solvent was removed by evaporation at 50° C. in a Buchi Rotavapor (Brinkmann Instruments, Westbury, N.Y.). The dried pyridine extract was extensively dialyzed against distilled water and then lyophilized. The resulting purified pyridine extract contained about 12% by weight of protein, about 12% by weight of sugar and about 45% of fatty acids. The extract was examined under an electron microscope and found to be free of contaminating whole cells and cell wall fragments. The yield of the pyridine-soluble extract was 9% (8.1 g.).

EXAMPLE 2

Preparation of Pyridine-Soluble Extract from *M. bovis* Strain BCG

*M. bovis* Strain BCG was grown and harvested in Sautons medium at 37° for 3 to 4 weeks to obtain a washed whole cell paste produced in the same manner disclosed in Example 1. 50 grams (wet weight) of the washed paste was then treated in the same manner as Example 1 to produce a yield of the pyridine-soluble extract of 7% (3.5 g.). The extract contained 15% by weight of protein, 10% by weight of sugar and 52% by weight of fatty acids.

The pyridine soluble extract in combination with TDM and ACP in a pharmaceutically acceptable medium is significantly effective in the treatment of animal tumors to obtain total regression of the tumor in most cases.

What is claimed is:

1. A pharmaceutical composition for treating tumors selected from the group of bovine squamous cell carcinoma, bovine fibrosarcoma, equine sarcoid, equine melanoma, equine squamous cell carcinoma, canine mammary tumors, canine adenoma and canine melanoma, comprising an anti-tumor effective amount of a combination of an effective amount of a purified pyridine-soluble extract obtained from a microorganism selected from the group consisting of *M. bovis* BCG, *M. phlei*, *M. smegmatis*, *M. kansasii*, *Nocardia rubra*, *Corynebacterium diphtheriae* and *Corynebacterium parvum*, said extract obtained by:

(a) preparing a whole cell paste of said microorganism;
   (b) washing said paste;
   (c) treating said paste with pyridine to produce an extract and a residue;
   (d) removing said pyridine from said extract; and
   (e) dialyzing said dried extract to obtain said purified pyridine-soluble extract, an effective amount of trehalose dimycolate; and an effective amount of an acetone precipitated by-product of endotoxic glycolipids extracted with chloroform methanol; and a pharmaceutically acceptable carrier.

2. The composition of claim 1 wherein the amount of said extract is up to about 40 milligrams, the amount of trehalose dimycolate is up to about 6 milligrams, and the amount of said acetone precipitated by-product is up to about 20 milligrams.

3. The composition of claim 1 wherein said composition is in

4. The composition of claim 1 wherein said composition is in the form of an oil droplet emulsion.

5. The composition of claim 2 wherein the amount of said extract is between about 200 and 5000 micrograms, the amount of trehalose dimycolate is between about 50 and 1000 micrograms and the amount of said acetone precipitated by-product is between about 150 and 1000 micrograms.

6. A method of treating tumors selected from the group consisting of bovine squamous cell carcinoma, bovine fibrosarcoma, equine sarcoid, equine melanoma, equine squamous cell carcinoma, canine mammary tumors, canine adenoma and canine melamoma in warm blooded animals comprising administering an effective amount of the composition of claim 1 to said warm blooded animals by injection directly into the tumor.

7. The method of claim 6 further comprising injecting into said tumor said composition containing between about 375 and 2500 micrograms/milliliter of said pyridine-soluble extract product and between about 375 and 1250 micrograms/milliliter of each of trehalose dimycolate and said acetone precipitated by-product.

* * * * *